(12) United States Patent
Brunelle et al.

(10) Patent No.: US 6,727,370 B1
(45) Date of Patent: Apr. 27, 2004

(54) METHOD FOR PREPARING OXYDIPHTHALIC ANHYDRIDES USING BICARBONATE AS CATALYST

(75) Inventors: Daniel Joseph Brunelle, Burnt Hills, NY (US); Qing Ye, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/373,523

(22) Filed: Feb. 24, 2003

(51) Int. Cl.[7] ............. C07D 307/89; C07D 407/02

(52) U.S. Cl. .................................. 549/241

(58) Field of Search ........................ 549/241

(56) References Cited

U.S. PATENT DOCUMENTS

| | | | |
|---|---|---|---|
| 4,837,404 A | 6/1989 | Schwartz |
| 4,870,194 A | 9/1989 | Molinaro et al. |
| 4,948,904 A | 8/1990 | Stults |
| 5,021,168 A | 6/1991 | Molinaro et al. |
| 5,153,335 A | 10/1992 | Stults |
| 6,028,203 A | 2/2000 | Brunelle et al. |

*Primary Examiner*—Robert W. Ramsuer
*Assistant Examiner*—Golam M M Shameem
(74) *Attorney, Agent, or Firm*—Andrew J. Caruso; Patrick K. Patnode

(57) ABSTRACT

Oxydiphthalic anhydrides such as 4-oxydiphthalic anhydride are prepared by the reaction of a halophthalic anhydride with an alkali metal carbonate such as potassium carbonate in the presence of a catalyst system comprising an alkali metal bicarbonate such as potassium bicarbonate and a phase transfer catalyst, preferably a tetraarylphosphonium halide.

16 Claims, No Drawings

METHOD FOR PREPARING OXYDIPHTHALIC ANHYDRIDES USING BICARBONATE AS CATALYST

BACKGROUND OF THE INVENTION

This invention relates to the preparation of oxydiphthalic anhydrides, and more particularly to improved phase transfer catalyzed methods for such preparation.

Oxydiphthalic anhydrides, particularly 4,4'-oxydiphthalic anhydride, are important monomers for the preparation of polyetherimides having exceptionally high temperature performance and excellent solvent resistance. These properties are useful in high performance plastics applications such as advanced composites and electronic circuit materials.

A number of publications, chiefly of Occidental Chemical Corporation, describe the preparation of oxydiphthalic anhydrides by the reaction of halophthalic anhydrides with potassium carbonate. Such publications include U.S. Pat. Nos. 4,870,194, 5,021,168 and 5,153,335. Suitable reaction conditions include neat and solvent reactions and the presence of various catalysts, typically phase transfer catalysts such as tetraphenylphosphonium halides, fluorides such as potassium fluoride and cesium fluoride and carboxylic acids and their salts and hydrolysable esters. Many of these catalytic materials are relatively expensive or limited in their effectiveness, and product yields are often undesirably low. Moreover, numerous ambiguities are present in said publications regarding water content of the reaction mixtures and other conditions, making reproducibility questionable.

It is of interest, therefore, to provide a method for oxydiphthalic anhydride preparation which affords high yields and a minimum of by-products and which is consistently and reproducibly applicable.

SUMMARY OF THE INVENTION

The present invention enables the preparation of oxydiphthalic anhydrides with the use of readily available and relatively inexpensive catalytic materials. Said preparation consistently affords high yields of the desired product and is highly reproducible.

The invention is a method for preparing an oxydiphthalic anhydride which comprises contacting, under reactive and substantially anhydrous conditions, at least one halophthalic anhydride with at least one carbonate of the formula $M_2CO_3$ in the presence of catalytic proportions of at least one phase transfer catalyst and a bicarbonate of the formula $MHCO_3$, wherein M is an alkali metal.

DETAILED DESCRIPTION PREFERRED EMBODIMENTS

The oxydiphthalic anhydrides that may be prepared by the method of the invention include 4,4'-oxydiphthalic (hereinafter sometimes designated '4-ODPA"), 3,3'-oxydiphthalic and 3,4'-oxydiphthalic anhydrides. The organic reagents for these compounds are, respectively, 4-halophthalic, 3-halophthalic and a mixture of 3- and 4-halophthalic anhydrides. For commercial purposes, the preferred anhydride is generally 4-ODPA, and frequent reference to it will be made hereinafter, it should be understood, however, that one of the other isomers may be substituted for 4-ODPA where appropriate.

Any halogen may be present in the halophthalic anhydride. Most often the fluoro-, chloro- or bromophthalic anhydride is employed, with the chlorophthalic anhydride being preferred by reason of its relatively low cost and particular suitability.

The reaction producing 4-ODPA is with at least one carbonate of the formula $M_2CO_3$, in which M is an alkali metal such as sodium, potassium, rubidium or cesium. Mixtures of such carbonates may be employed. For optimum product yield, it is preferred to employ carbonates of alkali metals having an atomic number of at least about 19. Potassium carbonate is preferred.

Particle size of the carbonate can have an effect on product yield. Thus, powdered potassium carbonate has been shown to produce a higher yield of oxydiphthalic anhydride than granular potassium carbonate in the same time period. However, it has been found that powdered potassium carbonate is more difficult to dry than the granular form. By reason of the deleterious effect of water on the reaction, it is important if powdered potassium carbonate is used that it first be thoroughly dehydrated.

Contact between the halophthalic anhydride and the carbonate is under reactive conditions, generally including temperatures in the range of about 120–250° C. and preferably about 170–250° C., atmospheric pressure and a molar ratio of halophthalic anhydride to carbonate in the range of 1.4–3.0:1, preferably 2.04–2.22:1. Optimum theoretical yields require a molar ratio of 2:1, but it has been discovered that a side reaction producing the corresponding hydroxyphthalic anhydride can occur under some conditions at a substantial reaction rate if the molar ratio is 2:1 or lower. In the preferred range of 2.04–2.22:1, the rate of the side reaction is negligible and optimum conditions for obtaining the desired product in high yield are attained.

The reaction may be performed in the absence or in the presence of at least one solvent. In various embodiments it is preferred that the reaction be conducted in a solvent. While dipolar aprotic solvents may be used, their use is generally not advisable since they can promote side reactions and the formation of colored by-products. In various embodiments suitable solvents have a boiling point above about 120° C., preferably above about 150° C. and more preferably above about 180° C. Suitable solvents of this type include, but are not limited to, ortho-dichlorobenzene, para-dichlorobenzene, dichlorxtoluene, 1,2,4-trichlorobenzene, diphenyl sulfone, phenetole, anisole and veratrole, and mixtures thereof. It is more preferred that chlorinated aromatic liquids be employed as solvents, examples of which include, but are not limited to, o-dichlorobenzene, 2,4-dichlorotoluene and 1,2,4-trichlorobenzene. 2,4-Dichlorotoluene is often most preferred since its use minimizes reaction time and product decomposition. In the case of some solvents, such as o-dichlorobenzene, the proportion of phase transfer catalyst can be increased and/or the reaction can be run at superatmospheric pressure to permit higher temperatures and higher reaction rates.

The reaction mixture should be substantially anhydrous, the term "substantially anhydrous" denoting a total water content of less than about 50, preferably less than about 20 and most preferably less than about 10 ppm by weight. Any water present above this amount can inhibit the reaction, irrespective of its source. Traces of water may be present in either of the reagents and also in the bicarbonate, and they should be carefully removed by drying before beginning the reaction. Drying can be achieved by methods known in the art liquid reagents and solvents can be dried by distillation and/or by contact with molecular sieves, and solid materials such as the carbonate and bicarbonate by heating in an oven, most often under vacuum.

In this connection, it should be noted that the present invention differs significantly from the reaction disclosed in the aforementioned U.S. Pat. No. 5,153,335. That patent is inconsistent as to the proportion of water present in the reaction mixture. Claim 1 requires a substantially anhydrous medium, but the specification states that the water content is in the range of 0.05–0.5 mole percent, supposedly corresponding to a weight proportion in the range of 100–2,000 ppm. By calculation, however, 100–2,000 ppm is equivalent to 0.2–4.0 mole percent. Thus, it is very difficult to draw any conclusions about the amount of water preferred according to the patent, or even whether the presence of water is contemplated.

In one embodiment of the present invention, a bicarbonate having the formula $MHCO_3$, where M is as previously defined, is part of the catalyst system, which also includes a phase transfer catalyst. The preferred bicarbonate is potassium bicarbonate. Preferred phase transfer catalysts are those that are stable at the prevailing reaction temperature. These include quaternary phosphonium halides, exemplified by tetraalkylphosphonium halides including, but not limited to, tetra-n-butylphosphonium chloride and tetra-n-butylphosphonium bromide; mixed alkylaryl tetrasubstituted phosphonium halides, including, but not limited to, butyltriphenyl phosphonium bromide; and tetraarylphosphonium halides including, but not limited to, tetraphenylphosphonium bromide. The tetraarylphosphonium halides are preferred, with the bromides being most preferred. When the catalyst system includes a bicarbonate, the use of hexaalkylguanidinium halides as phase transfer catalysts is not preferred since they tend to slow the reaction, decreasing yield over similar time periods in comparison with reactions employing quaternary phosphonium halides.

Optimum catalyst proportions will depend to some extent on the identity of the solvent and other factors. For the most part, an amount of phase transfer catalyst is in the range of about 0.2–10.0; preferably 0.4–2.0, mole percent based on halophthalic anhydride. As noted hereinabove, higher proportions within this range may be preferred when the solvent is o-dichlorobenzene than when it is 2,4-dichlorotoluene. Bicarbonate levels are typically in the range of 0.2–1.0 mole percent based on halophthalic anhydride.

When the reaction between halophthalic anhydride and carbonate is complete, the product may be isolated by conventional techniques. It is often convenient to merely cool the solution in solvent after filtration while hot, whereupon the desired oxydiphthalic anhydride precipitates and may be removed by filtration.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

All parts and percentages are by weight unless otherwise designated Chemicals and solvents were reagent grade, and were carefully dried and otherwise used without purification. Solvents were dried over activated 3 Å molecular sieves before use. Granular potassium carbonate was dried in a vacuum oven overnight before use. Analysis was performed by contacting the reaction mixture with n-butylamine and acetic acid to convert anhydrides to the corresponding N-(n-butyl)imides, followed by high pressure liquid chromatography using a tetrahydrofuran-water mixture as the eluting solvent.

EXAMPLE 1

4-Chlorophthalic anhydride (16 grams [g], 87.7 mmol) was weighed into a 50 milliliter (ml) round-bottomed flask containing about 17 ml of o-dichlorobenzene. The mixture was heated at reflux for 0.5 hour in a nitrogen atmosphere with distillation of solvent until less than 20 ppm of water was present, whereupon about 7 ml of solvent had been removed. Tetraphenylphosphonium bromide, 400 milligrams (mg) (0.95 mmol) was added with stirring, whereupon the solution turned yellow. Potassium bicarbonate, 22 mg (0.22 mmol), was added, followed by 5.45 g (39.5 mmol) of potassium carbonate in a stepwise fashion over 5–10 minutes. The mixture was heated at reflux (bath temperature 200° C.) after the first addition of $K_2CO_3$. The mixture was heated under reflux for 17 hours after the final addition of $K_2CO_3$. At the end of the reaction, additional o-dichlorobenzene was added to form a 10% solution and the by-product KCl was removed by filtration while hot. The filtrate was cooled to room temperature, whereupon the desired 4,4'-ODPA precipitated and was collected by suction filtration. 11.56 g of slightly pink-colored powder was obtained. Recrystallization from o-dichlorobenzene afforded 10.87 g of product (80% of theoretical) as an off-white powder, m.p. 225–226° C.

EXAMPLE 2

The procedure of Example 1 was repeated, substituting 2,4-dichlorotoluene for the o-dichlorobenzene and reducing the tetraphenylphosphonium bromide amount to 200 mg. Reflux time was 7.5 hours after the final addition of $K_2CO_3$. Product yield was 82% of theoretical.

EXAMPLE 3

4-Chlorophthalic anhydride (4800 g, 26.3 moles) and 7836 g of o-dichlorobenzene were charged to a 3.8 liter (L) stainless steel reactor. The mixture was heated at reflux for about 0.5 hour in a nitrogen atmosphere and 1020 g of o-dichlorobenzene was removed to dry the system. With stirring, 120 g (0.29 mole) of tetraphenylphosphonium bromide was added. After mixing, 6.6 g (0.066 mole) of potassium bicarbonate was added, followed by 1650 g (11.95 moles) of potassium carbonate in 7 portions. The mixture was heated under reflux for 27 hours after the last addition of $K_2CO_3$ and periodically analyzed. About 60% of conversion was achieved at this point. To make sure that the reaction went to completion, an additional 50 g (0.119 mole) of tetraphenylphosphonium bromide was added. The mixture was heated overnight, whereupon conversion reached about 90%.

o-Dichlorobenzene, 39,500 g, was added to dilute the reaction mixture and the temperature was brought to 165° C. A hot filtration was performed through a 1-micron filter bag. The filtrate was cooled to room temperature and the desired 4,4'-ODPA was collected in about 80% crude yield and 95% purity. Recrystallization from o-dichlorobenzene gave pure product, m.p. 225–226° C.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. A method for preparing an oxydiphthalic anhydride which comprises contacting, under reactive and substantially anhydrous conditions, at least one halophthalic anhydride with a carbonate of the formula $M_2CO_3$ in the presence of catalytic proportions of at least one phase transfer catalyst and a bicarbonate of the formula $NHCO_3$, wherein M is an alkali metal.

2. The method according to claim 1 wherein the halophthalic anhydride is 3-chlorophthalic anhydride, 4-chlorophthalic anhydride or a mixture thereof.

3. The method according to claim 2 wherein the halophthalic anhydride is 4-chlorophthalic anhydride.

4. The method according to claim 1 wherein M has an atomic number of at least 19.

5. The method according to claim 4 wherein M is potassium.

6. The method according to claim 5 wherein the carbonate is powdered.

7. The method according to claim 1 wherein a solvent is also present.

8. The method according to claim 7 wherein the solvent is at least one member selected from the group consisting of ortho-dichlorobenzene, para-dichlorobenzene, dichlorotoluene, 2,4-dichlorotoluene, 1,2,4-dichlorobenzene, diphenyl sulfone, phenetole, anisole and veratrole, and mixtures thereof.

9. The method according to claim 8 wherein the solvent is o-dichlorobenzene, 2,4-dichlorotoluene or 1,2,4-trichlorobenzene.

10. The method according to claim 1 wherein the phase transfer catalyst is a quaternary phosphonium halide.

11. The method according to claim 10 wherein the phase transfer catalyst is tetraphenylphosphonium bromide.

12. The method according to claim 1 wherein a molar ratio of halophthalic anhydride to carbonate in the range of 1.4–3.0:1 is employed.

13. The method according to claim 1 wherein a proportion of bicarbonate in the range of 0.2–1.0 mole percent based on halophthalic anhydride is employed.

14. The method according to claim 1 wherein a proportion of phase transfer catalyst in the range of 0.2–10.0 mole percent based on halophthalic anhydride is employed.

15. The method according to claim 1 wherein a temperature in the range of about 120–250° C. is employed.

16. A method for preparing a 4-oxydiphthalic anhydride which comprises contacting, in a solvent with boiling point greater than about 150° C. under substantially anhydrous conditions and at a temperature in the range of about 120–250° C., 4-chlorophthalic anhydride with potassium carbonate in the presence of catalytic proportions of tetraphenylphosphonium bromide and potassium bicarbonate, the molar ratio of 4-chlorophthalic anhydride to potassium carbonate being in the range of 2.04–2.22:1 and the proportions of bicarbonate and phase transfer catalyst being in the ranges of 0.2–1.0 and 0.4–2.0 mole percent respectively, based on 4-chlorophthalic anhydride.

* * * * *

UNITED STATES PATENT AND TRADEMARK OFFICE
CERTIFICATE OF CORRECTION

PATENT NO. : 6,727,370 B1  Page 1 of 1
DATED : April 27, 2004
INVENTOR(S) : Brunelle et al.

It is certified that error appears in the above-identified patent and that said Letters Patent is hereby corrected as shown below:

Column 5,
Line 7, please replace "NHCO3" with -- MHCO3 --.

Signed and Sealed this

Fifteenth Day of February, 2005

JON W. DUDAS
*Director of the United States Patent and Trademark Office*